(12) United States Patent
Lochmann et al.

(10) Patent No.: US 11,414,370 B2
(45) Date of Patent: Aug. 16, 2022

(54) PROCESS FOR PREPARING POLYGLYCEROL ESTER OF FATTY ACIDS

(71) Applicant: IOI OLEO GMBH, Hamburg (DE)

(72) Inventors: Dirk Lochmann, Deutschland (DE); Sebastian Reyer, Deutschland (DE); Michael Stehr, Deutschland (DE)

(73) Assignee: IOI OLEO GMBH, Hamburg (DE)

( * ) Notice: Subject to any disclaimer, the term of this patent is extended or adjusted under 35 U.S.C. 154(b) by 0 days.

(21) Appl. No.: 16/965,426

(22) PCT Filed: Dec. 11, 2018

(86) PCT No.: PCT/DE2018/000363
§ 371 (c)(1),
(2) Date: Jul. 28, 2020

(87) PCT Pub. No.: WO2020/119839
PCT Pub. Date: Jun. 18, 2020

(65) Prior Publication Data
US 2021/0292269 A1    Sep. 23, 2021

(51) Int. Cl.
*C07C 67/08*  (2006.01)
*B01J 31/12*  (2006.01)
*C07C 67/60*  (2006.01)

(52) U.S. Cl.
CPC .............. *C07C 67/08* (2013.01); *B01J 31/12* (2013.01); *C07C 67/60* (2013.01)

(58) Field of Classification Search
CPC ......... C07C 67/08; C07C 67/60; C07C 69/33; B01J 31/12
See application file for complete search history.

(56) References Cited

U.S. PATENT DOCUMENTS

| | | | |
|---|---|---|---|
| 4,011,251 A | 3/1977 | Tjurin et al. | |
| 6,620,904 B2 * | 9/2003 | Lemke | C07C 67/08 528/275 |
| 2006/0240194 A1 | 10/2006 | Lemke | |

FOREIGN PATENT DOCUMENTS

| | | |
|---|---|---|
| DE | 4005819 A1 | 8/1991 |
| DE | 4101431 A1 | 7/1992 |
| EP | 0451461 A2 | 10/1991 |
| WO | 0236534 A2 | 5/2002 |
| WO | 2004041769 A1 | 5/2004 |
| WO | 2011098315 A1 | 8/2011 |
| WO | 2015036090 A1 | 3/2015 |

OTHER PUBLICATIONS

International Search Report based on PCT/DE2018/000363 dated Aug. 21, 2019.
Behrens, H., et al. "Synthese, Charaktensierung und Applikation von Polyglycerolen und Polyglycerolfettsaureestern," Die Nahrung, vol. 28, No. 8, 1984, pp. 815-835 (Abstract).

* cited by examiner

*Primary Examiner* — Yevgeny Valenrod
*Assistant Examiner* — Blaine G Doletski
(74) *Attorney, Agent, or Firm* — Miles & Stockbridge P.C.; Ajay Jagtiani

(57) ABSTRACT

A process is described for the preparation of polyglycerol fatty acid esters from a reaction mixture to which a metallic catalyst is added, as well as to a method for the purification of an intermediate synthesis product which contains excess fatty acid in addition to polyglycerol fatty acid esters. Compared with the prior art, a significantly improved yield and a higher process speed is obtained along with more economic use of raw materials, auxiliary materials, solvents and energy.

3 Claims, No Drawings

PROCESS FOR PREPARING POLYGLYCEROL ESTER OF FATTY ACIDS

CROSS-REFERENCE TO RELATED APPLICATIONS

This application is a National Stage of International Application No. PCT/DE2018/000363 filed on Dec. 11, 2018, which is hereby incorporated by reference in its entirety.

A process is described for the preparation of polyglycerol fatty acid esters from a reaction mixture to which a metallic catalyst is added, as well as a method for the purification of an intermediate synthesis product which contains excess fatty acid in addition to polyglycerol fatty acid esters. Compared with the prior art, a significantly improved yield and a higher process speed is obtained along with more economic use of raw materials, auxiliary materials, solvents and energy.

Polyglycerol fatty acid esters, abbreviated to PGE, have been and are already used industrially, for example as emulsifying agents in the food and cosmetics industry, as a component of rust protection agents, as plasticizers in the textile industry or in insecticides. Recently, application possibilities have arisen in the formulation of pharmaceuticals, wherein here, the preferred preparation is by syntheses which do not use potentially toxic starting materials and do not generate toxic intermediate products and by-products.

The simplest polyglycerols which can form the basic structure of PGEs are linear and branched diglycerols with the empirical formula $C_6O_5H_{14}$, which can be synthesized on an industrial scale and in a known manner, for example by reacting glycerol with 2,3-epoxy-1-propanol under basic catalysis with the formation of ether bonds, or by thermal condensation under base catalysis, wherein the fraction containing mainly diglycerols can subsequently be separated.

Diglycerols can occur in three different structurally isomeric forms, namely in the linear form, in which the ether bridge is formed between the respective first carbon atoms of the two glycerol molecules involved, in the branched form, in which the ether bridge is formed between the first carbon atom of the first and the second carbon atom of the second glycerol molecule employed, and in a nucleodendrimeric form, in which the ether bridge is formed between the respective second carbon atoms. In the case of the condensation of two glycerol molecules catalysed by an alkali, up to approximately 80% occurs in the linear form and up to approximately 20% in the branched form, while only a very small quantity of the nucleodendrimeric form is produced.

In the case of esterification with fatty acids, polyglycerols containing more than two glyceryl units may also be used. In general, the polyglycerols are abbreviated to "PG" and an integer n is added as a suffix, which provides the number of polyglyceryl units, i.e. "$PG_n$". As an example, triglycerols are written as $PG_3$ and have the empirical formula $C_9O_7H_{20}$. Complete esterification with a fatty acid, for example with stearic acid, should now take place at all of the free hydroxyl groups of the $PG_n$ molecule. In the case of a linear $PG_3$, then this would take place at the first and second carbon atoms of the first glyceryl unit, at the second carbon atom of the second glyceryl unit and at the second and third carbon atoms of the third glyceryl unit. The empirical formula for this example is therefore given as $C_9O_7H_{15}R_5$, wherein each R represents a fatty acid residue, in the selected example with the empirical formula $C_{18}OH_{35}$.

In the case of polyglycerol fatty acid esters, a distinction must be made between partial esters and full esters. The established abbreviation for polyglycerols esterified with saturated unbranched fatty acids is the designation PG(n)-Cm full ester or, as appropriate, PG(n)-Cm partial ester, wherein the "n" in parentheses, in similar manner to the designation of the polyglycerols, gives the number of glyceryl units contained in the molecule and m represents the number of carbon atoms of the saturated fatty acid used for the esterification reaction. Thus, the "n" represents the number of glyceryl units with the empirical formula $C_3O_2H_5R$, wherein R may represent a fatty acid residue or the hydrogen atom of a free hydroxyl group. "PG(2)-C18 full ester" would therefore describe a polyglycerol fatty acid full ester with the empirical formula $C_{78}O_9H_{150}$. In the case of the PG(n)-Cm-partial ester, the number of fatty acid residues is averaged, whereupon at the same time, the empirical formula provides the fraction with the esterification variation which is most present in the majority. A more exact designation of the polyglycerol fatty acid partial ester is provided by the additional provision of the hydroxyl value, which is a measure of the non-esterified hydroxyl group content and thus provides information regarding the degree of esterification of the partial ester. Presumably for steric reasons, the esterification reactions in this case occur preferentially from the outside to the inside. Thus, initially, the hydroxyl groups which are esterified are those which allow the fatty acid residue the highest degree of freedom. The first esterification reaction at a linear polyglycerol then preferentially takes place at the hydroxyl group of a first carbon atom of a marginal polyglyceryl unit located at one end, then the second esterification reaction takes place at a hydroxyl group of a first carbon atom of a marginal polyglyceryl unit at the other end. Next, the hydroxyl groups at carbon atom positions immediately adjacent to positions which have already been esterified are esterified, and so on.

The synthesis of PG full esters differs from the synthesis of PG partial esters in particular in that in the former, as much fatty acid necessarily has to be provided to the polyglycerol to be esterified which allows all of the hydroxyl groups of the polyglycerol which is present to be esterified. As an example, one mole of linear diglycerol should theoretically be esterified with four moles of fatty acid in order to obtain a PG full ester, because each molecule of diglycerol has four free hydroxyl groups which can therefore be esterified. In practice, the use of a molar excess over the theoretically necessary quantity for full esterification is advantageous, optionally reduced in accordance with a reaction-dictated reduction in the number of free hydroxyl groups in order to keep the reaction time to complete esterification as short as possible. A reaction-dictated reduction of this type may arise because of sublimation processes through heating of the reaction mixture.

The term "fatty acids" as used here should be understood to mean aliphatic monocarboxylic acids, preferably containing 6 to 22 carbon atoms, which are preferably unbranched and saturated and have an even number of carbon atoms, but they may also contain an odd number, be branched and/or unsaturated. Particularly preferably, for the preparation of the polyglycerol fatty acid full esters to be purified, unbranched, saturated fatty acids containing 16, 18, 20 or 22 carbon atoms are used, i.e. palmitic, stearic, arachidic or behenic acid.

In the case of the preparation of the aforementioned PG(n)-Cm full esters, the excess fatty acid which is employed during the synthesis has to be removed following the esterification reaction which is as complete as possible.

In this regard, the problem arises that distillation as a method is not possible because of the effort involved and the high boiling points of the participating components, because the reaction products are heavily thermally stressed and could not be expected to reach the targeted acid value of less than 1 mg KOH/g. Instead, refining with dilute aqueous sodium or potassium hydroxide is usually carried out, during which the corresponding sodium or potassium salt of the fatty acid is also formed, generally speaking as soaps. The soaps formed are then washed with water, usually in several steps as described, inter alia, by Michael Bockisch in the "Handbuch der Lebensmitteltechnologie" [Food Technology Manual], Ulmer Verlag, Stuttgart 1993, p. 484ff. The problem in this case is that soaps act as emulsifiers and the substantial emulsion formation that occurs in this leads to loss of polyglycerol fatty acid ester yields, which as a rule amount to more than 50%. As soon alkaline refining has been carried out to an acid value of less than 3.0 mg KOH/g, however, so much soap is formed that the emulsion-related loss of yield can no longer be tolerated.

As an alternative to refining using dilute aqueous hydroxides, as disclosed in DE 41 01 431 A1, dry refining has also been attempted in which, after the complete esterification reaction, the reaction product containing excess fatty acid is supplemented with sodium carbonate decahydrate or sodium hydrogen carbonate as a refining agent in order to then mechanically separate the soaps which have been formed from the PG full esters. Because of the fact that the reaction can only take place at the interfaces between the fatty acid and refining agent, the degree of conversion here is highly dependent on the granulometry and intensity of mixing. In this method, the soaps and excess refining agent are filtered off using filter auxiliaries such as bentonites, for example, with concomitant and unwanted yield losses of more than 12%. Thus, the objective is to make both the synthesis conditions for the preparation of polyglycerol fatty acid esters more efficient for pharmaceutical purposes using non-toxic components of the respective reaction mixture, and also to separate any excess fatty acids during the course of a post-synthesis purification as quantitatively as possible and at the same time to raise the yield to more than 90%.

The objective is achieved as regards the synthesis conditions by means of a process as claimed in claim 1, and as regards the purification by means of a method as claimed in claim 3; advantageous embodiments are defined in the respective dependent claims.

A process which comprises a synthesis method is proposed for the preparation of polyglycerol fatty acid esters from a reaction mixture which contains fatty acid and polyglycerol. In this regard, a catalyst is added to the reaction mixture which has at least one metallic compound which contains at least the metals manganese, zinc, cobalt or titanium such as, for example, the respective tetrahydrates of zinc acetate, cobalt acetate or manganese (II) acetate. A high efficiency as regards the degree of conversion and rate of reaction is offered by non-toxic tetrabutyl titanate, which is preferred in accordance with the invention for the synthesis of polyglycerol fatty acid full esters and it can also be used to increase the efficiency for the synthesis of PG(n)-Cm partial esters from polyglycerol and fatty acid. Because titanium is tetravalent, the n-butanol ligand sphere can be exchanged for up to four reagents which respectively have at least one reactive hydroxyl group. In this regard, the strong Lewis acid titanium (iv) acts as an activator for the reagents, which react with fatty acid to form the corresponding esters.

The removal from such an intermediate product of excess fatty acids which arise during the catalysed or non-catalysed synthesis of polyglycerol fatty acid esters, in particular of polyglycerol fatty acid full esters, in an intermediate product which is to be purified, by means of a method for the purification of polyglycerol fatty acid esters is also proposed, which intermediate product can be obtained, for example, from polyglycerol and fatty acid or derivatives thereof by carrying out a reaction method, wherein the preferably liquefied intermediate product which still contains excess fatty acid is refined with basic solution, preferably with dilute aqueous sodium or potassium hydroxide until fatty acid salts are formed and an acid value for the fatty phase of less than 1.0 mg KOH/g is obtained in order thereafter to advantageously undergo removal of the solvent, preferably by pressure reduction, which is preferably followed by a separation step for the separation of the fatty acid salts from the polyglycerol fatty acid ester by means of centrifuging, or alternatively by means of filtration. Surprisingly, it is possible to carry out a refining step to an acid value for the fatty phase of less than 1.0 mg KOH/g without compromising the yield, because removal of the solvent, which can preferably be carried out when aqueous refining agents are used by drying at approximately 100° C. and by reducing the pressure in steps to less than 20 mbar, rapidly destroys sufficient of the emulsion of polyglycerol fatty acid esters mediated by the fatty acid salts in the solvent. In this manner, the subsequent separation step can deliver a yield of polyglycerol fatty acid full esters of more than 90%. Advantageously, the separation step is carried out after the solvent removal in a temperature range in which the soaps have already partially solidified. In the reaction method, a direct esterification reaction is preferred which is initiated from a mixture of polyglycerol and fatty acid by heating.

The efficiency of the purification method may be increased by modification of the upstream reaction method for the intermediate product to be purified. In this regard, it has been shown to be advantageous for the polyglycerols and fatty acids employed to be at temperatures of approximately 80° C. and to melt them with the formation of a two-phase mixture, which surprisingly has no negative effects at all on the later yield or on the product properties of the polyglycerol fatty acid full ester, inter alia because the two-phase reaction mixture homogenizes during the course of the reaction method. Clearly, in addition, only one of the components of the reaction mixture could be introduced in the liquid form and liquefaction of the reaction mixture could be achieved heat exchange between the components.

Furthermore, the upstream reaction method may comprise the addition of a suitable catalyst with the aforementioned features, with the advantage that the excess fatty acid and thus the proportion of fatty acid to be removed from the intermediate product may be smaller without extending the reaction time.

The excess fatty acid necessary for the reaction method may also preferably be reduced by means of a drying step in which initially, the pressure applied to the reaction mixture is a pressure which is below normal pressure, of less than 20 mbar. Preferably, this drying step is carried out before adding a catalyst.

In order to obtain as quantitative a reaction of the starting products as possible, the reaction method preferably comprises a heating step in which the reaction mixture is heated to up to 235° C. at a pressure of 400 mbar. In this, the intended esterification reaction is initiated at approximately 200° C.

Furthermore for the subsequent purification method and for a small quantity of fatty acid in the intermediate product, during the reaction method the pressure of the reacted reaction mixture is advantageously reduced, during which the pressure on the reaction mixture is preferably reduced in steps from 400 mbar to below 50 mbar.

In addition, it has been shown that the purification method for polyglycerol fatty acid esters is particularly efficient when the intermediate product to be purified has a hydroxyl value of less than 20 mg KOH/g, preferably less than 10 mg KOH/g and particularly preferably less than 4 mg KOH/g, and at the same time an acid value of less than 15 mg KOH/g, preferably less than 10 mg KOH/g and particularly preferably less than 4 mg KOH/g. The low hydroxyl value compared with polyglycerol fatty acid partial esters indicates an almost complete esterification of the free hydroxyl groups of the polyglycerol employed, while the acid value is an indication of the quantity of excess fatty acid in the intermediate product.

For the purification of the polyglycerol fatty acid ester-containing intermediate product produced by the reaction method to succeed, advantageously, the steps of the method are carried out in the following sequence:
i) liquefaction step as claimed in ste i) of claim 1,
ii) drying step as claimed in step ii) of claim 1,
iii) heating step as claimed in step iv) of claim 1,
iv) pressure reduction as claimed in step v) of claim 1,
v) refining step as claimed in step vi) of claim 1,
vi) solvent extraction as claimed in step vii) of claim 1 or claim 3,
vii) separation step as claimed in step viii) of claim 1.

Advantageously, filtration may then be carried out using a 1 µm filter.

The quantity of fatty acid or fatty acid derivative used in the reaction mixture enables the process for the preparation of polyglycerol fatty acid esters to be controlled in a manner such that the catalysed synthesis method results either in polyglycerol fatty acid partial esters or in polyglycerol fatty acid full esters. If the reaction mixture contains a significant excess of polyglycerol-bonded hydroxyl groups compared with the carboxyl or carboxylate groups to be esterified, then a partial ester is produced. If, on the other hand, the reaction mixture contains at least one polyglycerol-bonded hydroxyl group for each of the carboxyl or carboxylate groups to be esterified, preferably an excess of such hydroxyl groups, then the catalysed synthesis method is orientated towards polyglycerol fatty acid full esters.

During the course of the preparation process, the synthesis method may advantageously be supplemented by the method for the purification of polyglycerol fatty acid esters from an intermediate product containing excess fatty acid. The addition of the catalyst during the synthesis method is carried out here both for syntheses orientated towards partial esters and also orientated towards full esters, preferably between the drying step discussed for the reaction method and the following heating step, the remaining sequence of the steps used in the reaction method remaining unchanged. Here again, subsequently, filtration may be carried out using a 1 µm filter, wherein the catalyst or its reaction products such as titanium dioxide when tetrabutyl titanate is used, for example, can be almost completely eliminated. However, the respective metal of the catalyst employed will still be detectable in the end product in trace quantities.

A process for the preparation of polyglycerol fatty acid esters from a reaction mixture comprising a synthesis method will now be described in more detail with the aid of two examples, wherein the first example concerns the preparation of partial esters and the second example concerns the preparation of full esters including purification in order to eliminate excess fatty acid.

EXAMPLE 1

PG(3)-C16/C18 Partial Ester 2700 g of PG(3), 2390 g of palmitic acid and 5590 g of stearic acid were placed in a reactor and melted at 80° C. After drying under vacuum (<20 mbar), 3.3 g of tetrabutyl titanate was added as the catalyst. The reaction mixture was heated up to 235° C. under a 400 mbar vacuum. The reaction was initiated beyond ~200° C. After reaching 400 mbar, the reaction pressure was reduced in steps to <50 mbar. Esterification was continued until an acid value of <1.0 mg KOH/g was obtained. The reaction time was 4 to 6 hours. The reaction time, which was shorter compared with the procedure without a catalyst, resulted in a significantly improved colour of the product. The single-phase PG(3)-C16/C18 partial ester obtained in this mariner was then filtered through a 1 µm filter and decanted. The catalyst here was almost completely removed, however the respective metal was still able to be detected in trace quantities.

EXAMPLE 2

PG(2)-C18 Full Ester 1580 g of PG(2) and 10700 g of stearic acid were placed in a reactor and melted at 80° C. After drying at less than 20 mbar pressure, 3 g of tetrabutyl titanate was added to the two-phase mixture which was obtained, as the catalyst. Next, the reaction mixture was heated up to 235° C. at a pressure of 400 mbar, whereupon the reaction was initiated at approximately 200° C. Next, the reaction pressure was reduced in steps to less than 50 mbar. Esterification was continued until a hydroxyl value of less than 4 mg KOH/g was obtained. At the same time, the acid value was usually 4 to 6 mg KOH/g, but could reach up to 15 mg KOH/g. The polyglycerol fatty acid full ester-containing intermediate product was then refined at 80° C. to 90° C. with aqueous 10.5% NaOH solution until an acid value of less than 1.0 mg KOH/g was obtained, and so fatty acid salts had been formed. Next, for the purposes of drying, starting from a pressure of 800 mbar, a stepwise reduction in pressure was carried out to less than 20 mbar at 100° C. The soap which was obtained was separated by centrifuging, or alternatively could be filtered off. The yield of single-phase PG full ester was now more than 90%. Prior to decanting, the PG full ester could be filtered off over a 1 µm filter. This almost completely eliminated the catalyst, however the respective metal was still able to be detected in trace quantities.

The invention claimed is:
1. A process for the preparation of polyglycerol fatty acid esters from a reaction mixture containing fatty acid and polyglycerol
characterized by
the following steps being carried out in the given sequence:
i) liquefaction step, in which melting of polyglycerol and fatty acid forms a two-phase reaction mixture,
ii) drying step, in which drying of the reaction mixture is carried out under vacuum, iii) addition of a catalyst to the reaction mixture which has at least one metallic compound containing at least manganese, zinc, cobalt or titanium,
iv) heating step, in which the reaction mixture is heated at a pressure of 400 mbar to 200° C. to 240° C.,
v) pressure reduction step, during which the pressure on the reaction mixture is reduced from 400 mbar in steps to less than 50 mbar,
vi) refining step with a basic solution, undergone by the reaction mixture until a fatty acid salt and a fatty phase are formed and in the fatty phase, an acid value of less than 1.0 mg KOH/g is obtained,
vii) solvent extraction step,
viii) separation step, in which a separation of the fatty acid salts from the polyglycerol fatty acid esters is carried out.

2. The process as claimed in claim 1, characterized in the metallic compound comprises tetrabutyl titanate.

3. The process as claimed in claim 1, characterized in that the solvent extraction step is carried out at 90° C. to 110° C. and at a pressure of less than 30 mbar.

* * * * *